(12) United States Patent
Menchaca et al.

(10) Patent No.: US 7,040,323 B1
(45) Date of Patent: May 9, 2006

(54) THIN FILM INTRAUTERINE DEVICE

(75) Inventors: Leticia Menchaca, Berkeley, CA (US); A. David Johnson, San Leandro, CA (US); Vikas Gupta, San Leandro, CA (US); Valery Martynov, San Francisco, CA (US)

(73) Assignee: Tini Alloy Company, San Leandro, CA (US)

( * ) Notice: Subject to any disclaimer, the term of this patent is extended or adjusted under 35 U.S.C. 154(b) by 235 days.

(21) Appl. No.: 10/638,282

(22) Filed: Aug. 7, 2003

Related U.S. Application Data

(60) Provisional application No. 60/402,418, filed on Aug. 8, 2002.

(51) Int. Cl.
*A61F 6/06* (2006.01)

(52) U.S. Cl. .................................... 128/833; 128/830

(58) Field of Classification Search ................ 128/830, 128/832, 833, 839
See application file for complete search history.

(56) References Cited

U.S. PATENT DOCUMENTS

| 3,351,463 | A | * | 11/1967 | Buehler et al. | ............. 148/426 |
| 3,620,212 | A | * | 11/1971 | Fannon et al. | ............. 128/839 |
| 3,918,443 | A | * | 11/1975 | Vennard et al. | ............ 128/836 |
| 5,061,914 | A | * | 10/1991 | Busch et al. | ................ 337/140 |
| 5,190,546 | A | * | 3/1993 | Jervis | .......................... 606/78 |

* cited by examiner

*Primary Examiner*—Henry Bennett
*Assistant Examiner*—Camtu Nguyen
(74) *Attorney, Agent, or Firm*—Richard E. Backus

(57) ABSTRACT

Contraceptive intrauterine devices made of thin film shape memory alloy materials. The devices are formed in three-dimensional shapes which contact uterus tissue of a human or other mammal to prevent conception. In certain embodiments, structural features such as tails, fenestrations, ridges or grooves are formed on the devices to enhance the contraceptive effect.

2 Claims, 2 Drawing Sheets

THIN FILM INTRAUTERINE DEVICE

CROSS-REFERENCE TO PRIOR APPLICATION

This application claims the benefit under 35 USC §119(e) of U.S. provisional application Ser. No. 60/402,418 filed Aug. 8, 2002.

BACKGROUND OF THE INVENTION 1.0 Field of Invention

This invention relates to contraceptive intrauterine devices (IUDs) and methods of preventing conception.

2.0 Description of the Related Art

Reproductive medicine is lagging in contraception technologies at a time when the world population is about to include the largest proportion of people of reproductive age ever. This invention introduces Nitinol thin film, a recent major advancement in material science and micro-electro-mechanic technology, to help resolve longstanding limitations in existing contraceptive intrauterine devices.

Intrauterine contraceptive devices (IUDs) are objects inserted into the uterus to prevent conception. Introducing an object into the uterus for birth control is an ancient discovery that has evolved to become the modern IUD. The use of such devices is based on the fact that the presence of a foreign object in the uterus discourages conception. IUDs have been invented of numerous and varied solid shapes and configurations. The most well known shapes are the ring, the "S", the coil or spiral, the "T" and the "T" with its transversal arms bent down. These devices are configured to occupy a significant portion of the uterine fundus in order to prevent expulsion through the cervical os, a lumen of a few millimeters in diameter.

Existing IUDs are most commonly inserted using an insertion tube and a complementary plunger. Prior to insertion, the extended arms of the "T" are manually inserted into the upper end of the insertion tube The tube is of sufficient diameter and malleability to constrain the extended arms of the device in a folded position during insertion. The loaded tube is pushed through the cervical os into the uterine cavity. When the desired position is achieved, the tube is withdrawn to release the IUD while the inner plunger is manually held stationary. Withdrawal of the insertion tube allows the arms of the "T" to unfold inside the uterus.

The required manual placement of the IUD in the insertion tube is disadvantageous because it is cumbersome, time consuming, and increases the possibilities of compromising the sterile field. Moreover, where the IUD must be positioned by human manipulation, there exists a hazard of erroneous placement that could reduce contraceptive effectiveness and may be a source of injury to the patient. Approximately 1 in 500 insertions of existing rigid IUDs cause perforation.

IUDs of some configurations must be positioned in the insertion tube by drawing back on the "tail," i.e., the string attached to the IUD for removal from the uterus. Such a method, however, is undesirable for an IUD having a "T" configuration since the arms would be drawn upwards. In some devices the folding of the IUD or placement in the insertion tube occurs after the initial placement of the insertion tube in the uterus, resulting in less control on placement position.

Attempts have been made to reduce the size of convention solid IUDs to allow use by younger women, but reducing size and surface area result in a less effective contraceptive and an increased rate of expulsion. The challenges in adapting these devices for use by nulliparous women include reducing size to reduce trauma and adverse reactions, while maintaining a large enough inert or medicated surface area to maximize effectiveness and a size sufficient to resist expulsion. These problems have limited the use of existing IUDs, especially in younger women.

The use of Nitinol is already well established in other areas of medicine and thin film devices are being developed to replace or expand these applications. For example, thin film devices are successfully used in neuro- and neurovascular surgery, where miniaturization, flexibility, and compliance are imperative to reach small vessels and to remove clots and block aneurisms.

OBJECTS AND SUMMARY OF THE INVENTION

It is a general object of the invention to provide a new and improved reversible contraceptive device and method for intrauterine use in humans and other mammals.

Another object to to provide a device and method of use of the type described which is relatively smaller, safer, less intrusive, easier to insert and remove, more comfortable, and less expensive to manufacture than currently available IUDs.

In its general concept, the invention provides contraceptive IUD devices, and methods of use, made from thin-film, shape memory alloy materials exhibiting superplasticity and shape memory at the internal body temperatures of humans and other mammals.

DESCRIPTION OF THE PREFERRED EMBODIMENTS

The contraceptive devices of the invention are comprised of thin films of a shape memory alloy (SMA), such as TiNi (also known as Nitinol). TiNi thin film is ~5 microns thick and has shape memory at human body temperature. At lower temperatures, the material is in its martensitic state, is highly ductile, and can withstand large deformations. At higher temperatures, such as that of the human body, the material undergoes a phase transformation to a more rigid austenitic state in which it is not easily deformed.

Figure 1:
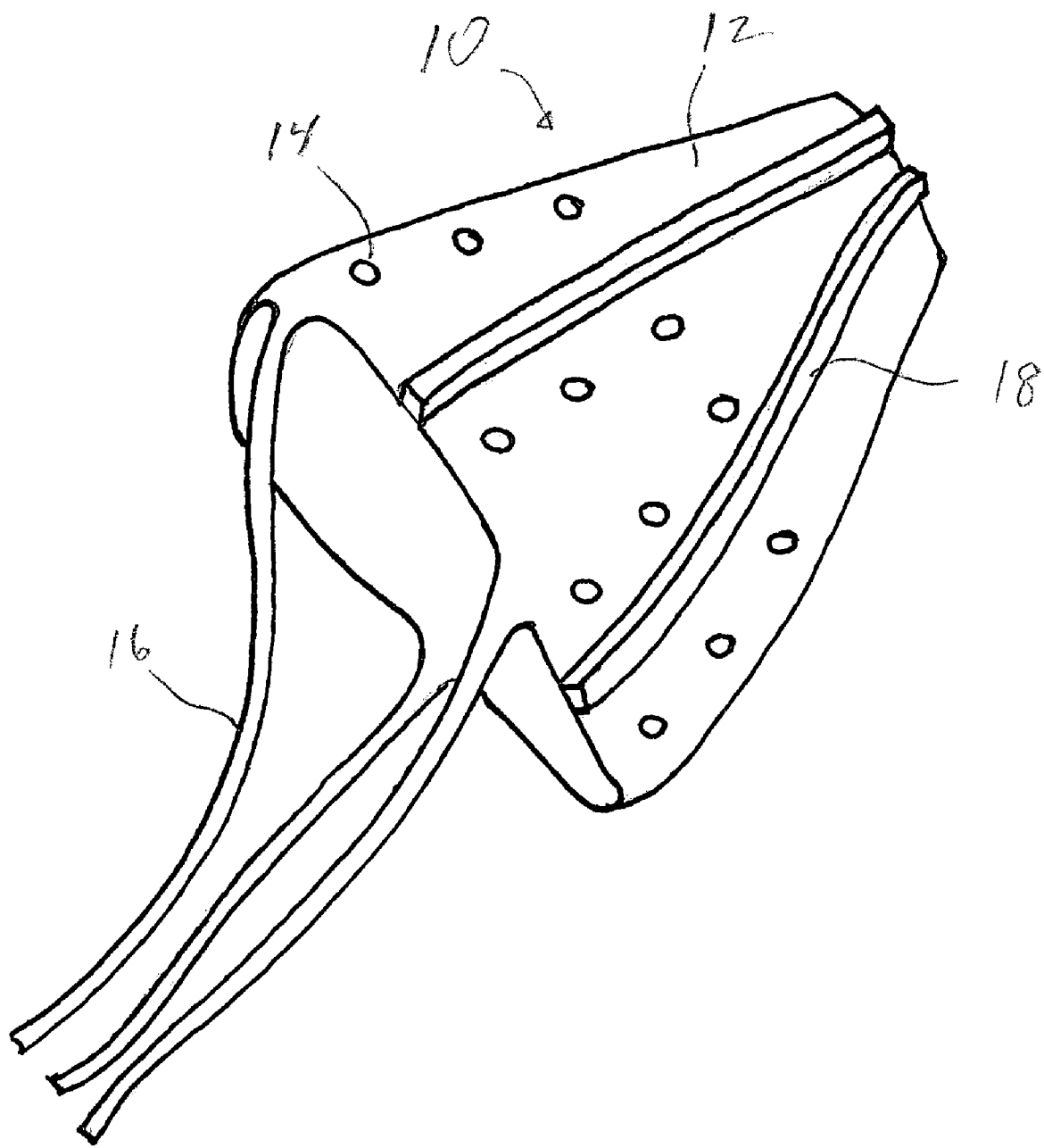
FIG. 1 is a perspective view of a device in accordance with one embodiment of the invention.
Figure 2:
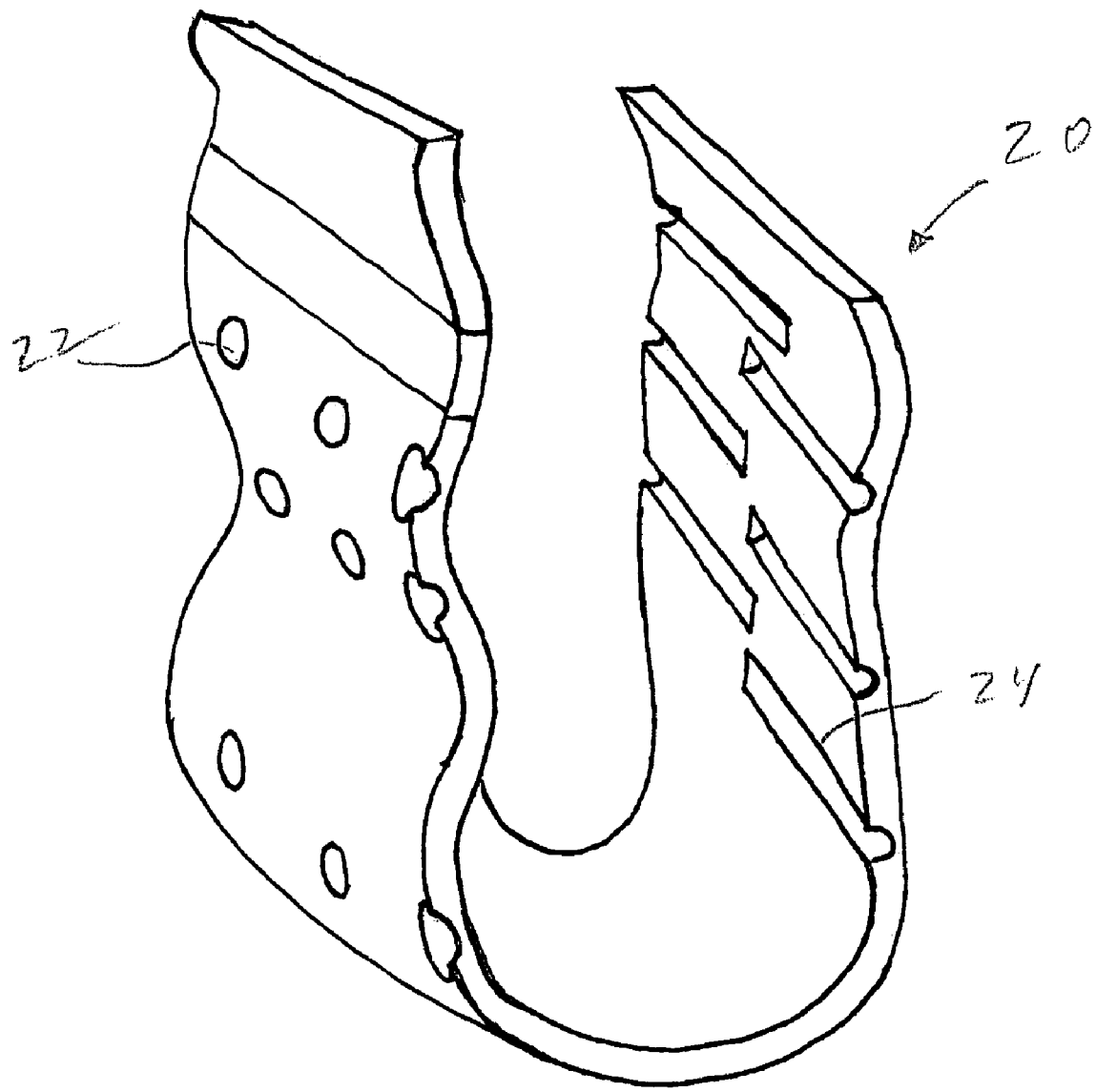
FIG. 2 is a perspective view of a device in accordance with another embodiment.

The contraceptive thin film IUD is a micro-fabricated three-dimensional object. FIG. 1 shows generally at 10 a thin film IUD device of frusto-conical shape in accordance with one preferred embodiment of the invention. FIG. 2 shows generally at 20 a thin film IUD device in a generally U-shape in accordance with another preferred embodiment. The invention contemplates that many other three-dimensional geometric shapes can be used for the device as long as the portions of the device surfaces make contact with the uterus wall sufficient to cause irritation of the wall. The irritation is believed to be the physiological reaction which prevents the mammal's egg from attaching to the wall, which would otherwise result in pregnancy. The uterus wall reacts and essentially "thinks" that conception has taken place when it has not.

Micro-electro-mechanical (MEM) techniques developed recently at TiNi Alloy Co permit the fabrication of seamless thin film three-dimensional structures that were impossible to fabricate in the past. Since this TiNi alloy film has a "body temperature phase transformation", then once inserted and released into the uterine cavity (temperatures ~37° C.), the thin film contraceptive expands within the uterus so that the film makes contact with the uterine walls with sufficient force to maintain its predetermined shape. The inherent elasticity of the thin film will also enable it to comply and move with the walls during contraction and relaxation of the uterine muscles.

By virtue of the characteristics of TiNi shape memory alloy, the IUD can be folded or rolled at low temperatures and introduced into the uterus within a very narrow tube, i.e. a catheter of less than 1 mm diameter. Once inside the uterus, the contraceptive foil is released from the catheter. The inherent properties of the shape memory alloy allow the IUD to automatically unfold and adopt a desired shape. The thin film contraceptive IUD can be manufactured, sterilized and pre-packed inside a catheter, minimizing contamination risks. The thin film IUDs can be micro-fabricated with appendages or tails. These would not be placed extracervically but would remain inside the uterus or cervix. Material for adding radio-opaque features to the contraceptive can also be used. A comparison between a regular IUD insertion tube and that used for a thin film contraceptive device is illustrated in FIG. 1.

Fabrication of the Device

In the invention three-dimensional shapes of thin films are fabricated using the general teachings of Busch et. al. U.S. Pat. No. 5,061,914, the disclosure of which is incorporated by this reference. Multiple layers of TiNi thin film and sacrificial material are sputter deposited sequentially on a polished and oxidized silicon wafer. The sacrificial material can be chromium, aluminum, copper, or TiCuSil, a material obtained through Wesgo Metals. Chromium is preferentially used as a sacrificial layer.

A thin chromium layer is sputter deposited on the oxidized silicon wafer using RF sputtering at argon pressure of about 2 milliTorr. The thickness of the deposited thin film can be 500 A or more. A thin layer of TiNi is sputter deposited on top of the chromium layer using DC sputtering at an argon pressure of about 2 milliTorr. The thickness of the deposited TiNi layer can be from 1 to 40 microns. A thin chromium layer is then sputter deposited on top of the device layer. Typical thickness of this layer is about 1000 A. This layer acts as a protective layer for the underlying TiNi layer during subsequent lithography steps and provides a sacrificial layer that in the final steps of fabrication is dissolved away chemically in order to selectively create a pocket between the two device layers.

Three-dimensional thin film shapes as shown in FIG. 1 require two photo masks (mask1 and mask2) with appropriate pattern designs. The design of mask1 determines the final three-dimensional shape of the device; e.g., solid triangles for cones, rectangles for cylinders, semicircles for hemispheres, etc. Mask2 contains designs for fenestration or any other surface patterns that may be needed for the final device. Mask1 is used to pattern the top sacrificial layer deposited on the wafer described above.

Micro-photolithography techniques are then followed. A thin layer of positive photo resist liquid is spin-coated on the above wafer at about 4000 rpm and baked at 90° C. in a clean room convection oven. Using an ultraviolet light mask aligner, the wafer and mask1 are aligned and the photo resist layer is UV exposed though the mask plate which transfers the patterns from mask1 on to the photo resist layer. The wafer with exposed photo resist is immersed in developer solution to selectively remove the exposed sections of the photo resist thus creating windows in the photo resist layer on the wafer. When immersed in a chemical etchant, these windows in the photo resist allow for the selective etching of the chromium layer. After patterning, the photo resist layer is chemically dissolved away by immersing in a solvent.

The wafer is loaded back into the sputtering chamber that is taken to high vacuum. In the chamber, the top exposed surface is sputter-etched to remove any contamination. Sputter-etch is a process similar to sputtering except that in the case of sputter-etch the argon ions are accelerated to the substrate surface rather than the target surface. Highly energetic argon ions when operated in "sputter-etch" mode also remove the undesired thin native oxide layer on the surface, which may have formed during the lithography process. Following sputter-etch, another layer of TiNi film followed by another layer of chromium are sputter deposited on the substrate. The resulting TiNi film is heat-treated at 500° C. in vacuum for crystallization so that the material exhibits the properties of shape memory and superelasticity.

Photo resist is spin coated again to pattern the layers with designs in mask2 using the photolithography steps described above. In this step, after etching the top chromium layer, the underlying TiNi layers are also chemically etched with the same mask design in order to define the device's outer features. This is followed by the complete removal of the photo resist layer. To separate the devices from the surface of the substrate, the whole wafer with patterned layers is immersed in a chemical etchant to completely dissolve the sacrificial layer. The etchant for this purpose should etch the sacrificial material selective to the device layer. This etching not only separates the devices from the substrate surface but also selectively creates an empty pocket between the two TiNi layers by etching away the chromium layer from between.

A pattern of fenestrations 14 (FIG. 1) or 22 (FIG. 2) can be formed in the TiNi layer. To create fenestration patterns, the photo resist layer is patterned using mask2, which contains the necessary fenestration patterns. The basic process sequence to fabricate thin film devices with fenestration patterns is the same as the one described above except for the added designs on mask2. As described above, after patterning the photo resist layer with fenestration patterns, the chromium and TiNi layers are patterned by chemical etching.

The released multi-layered thin film devices from the above steps are in planar form which may be of various size and shapes: triangular, rectangular, semicircular etc. These multi-layered thin film devices may then be transformed into their corresponding three-dimensional shapes 12 (FIG. 1) by inserting a stainless steel mandrel into the pocket between the TiNi layers and re-annealing them at 500° C. in vacuum. Re-annealing of the thin film device with an inserted mandrel causes shape-setting according to the shape of the mandrel. Conical and hemispherical thin film devices with appended tentacle-type tails 16 or ridges 18 (FIG. 1), or grooves 24 (FIG. 2) may also be fabricated using the same processes.

In planar deposition of TiNi to produce three-dimensional structures, multiple layers are deposited by planar sputtering, with intermediate sacrificial layers patterned selectively, producing structures that can be opened to produce cones, cylinders, and other shapes. Multiple alternating layers of TiNi film and Cr sacrificial layers are applied by sputtering alternatively from a TiNi target, patterning, depositing a sacrificial layer from a Cr target, patterning a second time, and depositing a second TiNi layer. The number of TiNi layers is not limited to two: more complex structures may be formed by iteration of this sequence.

During fabrication of three-dimensional nitinol thin film structures, a metal such as copper is added as an integral part of the device. This is accomplished either by electroplating or by sputter deposition depending on the design of the finished film contraceptive product. The tails 16 (or strings, ribbons etc.) can be formed in the device as integral features rather than attached or welded onto it. The tails can function as features for retrieval of the device, similar to the regular IUD tail, or as the medicated or contraceptive agent (copper) carrier.

The invention claimed is:

1. A method of preventing conception in a human or other mammal comprising the steps of providing a device insertable into a mammalian uterus having an inner wall controlled by uterine muscles, the device comprising a thin film of shape memory alloy material that, responsive to being heated to its crystalline phase-change transformation temperature, undergoes a phase change and resulting shape change from a martensitic elastic phase to an austenitic memory having a predetermined shape, placing the device in the uterus, and heating the device to the transformation temperature, the thin film have a thickness in the range of one to forty microns sufficient to enable the device in its austenitic memory shape to make contact with the inner wall and enable the device in the predetermined shape to move with the inner wall during contractions and relaxations of the uterine muscles.

2. A method as in claim 1, including the step of inserting the device into the uterus when the device is in the elastic phase, and enabling the device to change to the memory shape responsive to heat from the uterus.

* * * * *